United States Patent [19]

Lumma, Jr. et al.

[11] Patent Number: 4,545,995

[45] Date of Patent: Oct. 8, 1985

[54] SUBSTITUTED PHENYLALKENYL AMMONIUM SALTS AS ANTIARRHYTHIMC AGENTS

[75] Inventors: William C. Lumma, Jr., Pennsburg, Pa.; Ronald A. Wohl, Morris Plains, N.J.

[73] Assignee: Schering A.G., Berlin, Fed. Rep. of Germany

[21] Appl. No.: 513,144

[22] Filed: Jul. 12, 1983

[51] Int. Cl.⁴ .................. A61K 31/275; A61K 31/14; C07C 121/50; C07C 91/00

[52] U.S. Cl. ................................ 514/523; 564/157; 564/162; 514/620; 564/164; 564/165; 514/622; 564/218; 564/223; 514/617; 564/287; 564/288; 514/603; 564/289; 514/595; 514/821; 260/465 E; 260/465 D; 260/501.15; 549/416; 560/12; 560/13; 560/34; 560/37; 560/42; 562/430; 562/432; 562/439; 562/442; 562/451; 564/49; 564/51; 564/82; 564/83; 564/85; 564/86; 564/99; 564/153; 564/154; 564/155; 564/156

[58] Field of Search .......... 260/465 E, 465 D, 501.15; 564/288, 49, 51, 82, 83, 85, 86, 99, 153, 154, 155, 156, 157, 162, 164, 165, 218, 223, 287, 289; 424/329, 324, 322, 321, 317, 316, 309, 304; 560/12, 13, 34, 37, 42; 562/430, 432, 439, 442, 451

[56] References Cited

U.S. PATENT DOCUMENTS 4,289,787 9/1981 Molloy et al. ..................... 424/329

*Primary Examiner*—Nicky Chan
*Attorney, Agent, or Firm*—Elizabeth A. Bellamy; John L. White; I. William Millen

[57] ABSTRACT

The novel unsaturated arylalkyl ammonium salts described herein are useful as antiarrhythmic agents. A method of treating arrhythmia by increasing the refractoriness of cardiac tissue is provided, as well as pharmaceutical formulations containing such ammonium salts.

29 Claims, No Drawings

SUBSTITUTED PHENYLALKENYL AMMONIUM SALTS AS ANTIARRHYTHIMC AGENTS

FIELD OF THE INVENTION

This invention relates to novel ammonium salts and their use as antiarrhythmic agents. Specifically, this invention relates to novel unsaturated arylalkyl ammonium salts, their methods of manufacture, the pharmaceutical compositions containing them as active ingredients and the method of using them for the treatment of arrhythmia. A novel process for the production of clofilium is also disclosed.

GENERAL DESCRIPTION OF THE INVENTION

Composition-of-Matter Aspect

In its composition-of-matter aspect, this invention relates to novel unsaturated arylalkyl ammonium salts. Particularly, this invention relates to the novel compounds defined by the following formula:

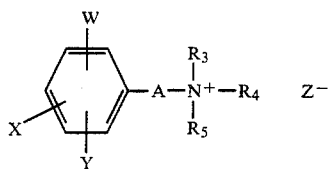

wherein A is

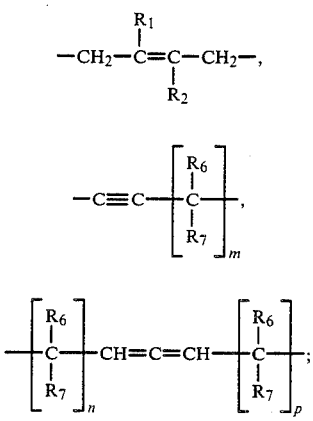

m is 2 or 3;
n is 0-3;
p is 1-3;
$R_1R_2=$ are both hydrogen, or both $C_1$–$C_2$ alkyl, or when taken together are —$(CH_2)_3$— or —$(CH_2)_4$— to form the cyclopentene or cyclohexene moieties;
$R_6R_7=$ hydrogen, $C_1$–$C_3$ alkyl;
$R_3R_4=C_1$–$C_4$ alkyl;
$R_5=C_5$–$C_{10}$ alkyl, phenyl $C_1$–$C_4$ alkyl, cycloalkyl (lower) alkyl;
W,X,Y = hydrogen, hydroxy, halogen, cyano, trifluoromethyl, carbamoyl, $C_1$–$C_4$ alkoxy, lower alkoxycarbonyl, N-lower alkylcarbamoyl, lower alkanoylamido, lower alkanesulfonamido, lower alkylsulfonyl, sulfamoyl, lower alkanesulfamoyl, N-lower alkylureido;
with the provisos that:

(a) only one of W, X and Y can be cyano or trifluoromethyl;
(b) only two of W, X and Y can simultaneously be hydroxy;
(c) at least one of W, X and Y is other than hydrogen; and $Z^-$ is a therapeutically acceptable anion.

In the above formula the use of the terms $C_1$–$C_4$, $C_5$–$C_{10}$, $C_1$–$C_3$ are meant to be straight or branched carbon chains. Cycloalkyl (lower) alkyl is meant to be a 3-7 membered cyclic system attached to which is a $C_1$–$C_4$ straight or branched chain alkyl group. The term halogen represents fluorine, chlorine, bromine and iodine. The terms lower alkoxy, lower alkane and lower alkyl are to represent $C_1$–$C_4$ straight or branched carbon chains. $Z^-$ as a therapeutically acceptable anion is defined as that which together with the ammonium cation forms a therapeutically acceptable salt. Commonly used anions include chloride, bromide, sulfate, p-toluenesulfonate, methanesulfonate, p-bromobenzenesulfonate, dihydrogenphosphate, carbonate, succinate, citrate, benzoate, acetate and the like. Preferred anions are bromide, chloride and dihydrogenphosphate.

Preferred classes of compounds embodied by this invention are those of the above general formula having one of more of the following characteristics:

(a) A is a 4 carbon chain
(b) Two of W, X, or Y are hydrogen
(c) One of W, X, or Y is halogen
(d) One of W, X, or Y is lower alkanesulfonamido
(e) One of W, X, or Y is N-lower alkylureido
(f) One of W, X, or Y is sulfamoyl
(g) $R_5$ is $C_5$–$C_{10}$ alkyl
(h) $R_3$ and $R_4$ are methyl or ethyl Still more preferred compounds of this invention of those defined as having one or more of the following characteristics:

(i) A is —$CH_2$—$CH$=$CH$—$CH_2$—
(j) W and Y are hydrogen and X is in the para position
(k) X is chlorine
(l) X is methanesulfonamido
(m) X is 3-methyl-1-ureido
(n) X is sulfamoyl
(o) $R_5$ is $C_7$ alkyl
(p) $R_3$ and $R_4$ are each ethyl
(q) $Z^-$ is chloride or dihydrogenophosphate The following are some of the compounds which exemplify various aspects of the invention described herein.

(1) 4-(4-chlorophenyl)-N,N-diethyl-N-heptyl-2-buten-1-aminium dihydrogenphosphate.
(2) N,N-diethyl-N-heptyl-4-(4-trifluoromethylphenyl)-2-buten-1-aminium chloride.
(3) N,N-diethyl-N-heptyl-4-(4-sulfamoylphenyl)-2-buten-1-aminium chloride.
(4) 4-(4-cyanophenyl)-N,N-diethyl-N-heptyl-2-buten-1-aminium chloride.
(5) N,N-diethyl-N-heptyl-4-(4-methoxycarbonylphenyl)-2-buten-1-aminium chloride.
(6) N,N-diethyl-N-heptyl-4-(4-methylsulfonylphenyl)-2-buten-1-aminium chloride.
(7) 4-(3-chlorophenyl)-N,N-diethyl-N-heptyl-2-buten-1-aminium chloride.
(8) 4-(2-chlorophenyl)-N,N-diethyl-N-heptyl-2-buten-1-aminium chloride.
(9) N,N-diethyl-N-heptyl-4-(4-methanesulfonamidophenyl)-2-buten-1-aminium chloride.
(10) 4-(2,3-dichlorophenyl)-N,N-diethyl-N-heptyl-2-buten-1-aminium 4-methylbenzenesulfonate.

(11) 4-(4-chlorophenyl)-N,N-diethyl-N-heptyl-2,3-dimethyl-2-buten-1-aminium chloride.
(12) 4-(4-chlorophenyl)-N,N-diethyl-N-heptyl-3-butyn-1-aminium chloride.
(13) N,N-diethyl-N-heptyl-4-[4-(3-methyl-1-ureido)-phenyl]-2-buten-1-aminium chloride.
(14) (E)-4-(4-chlorophenyl)-N,N-diethyl-N-heptyl-2-buten-1-aminium dihydrogenphosphate.
(15) (Z)-4-(4-chlorophenyl)-N,N-diethyl-N-heptyl-2-buten-1-aminium 4-methylbenzenesulfonate.

Among the compounds defined by the above formula, there exists when A is

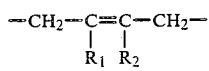

a site for geometric isomerism; such cis/trans isomers are considered to be part of this invention.

Process Aspect

In general, the novel compounds of this invention may be prepared by various processes and reactants known in the art.

Generally, in order to produce a compound according to Formula I wherein A is defined as

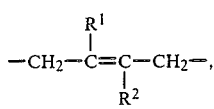

(a) a suitably substituted aniline is diazotized and then
(b) reacted in a Meerwein arylation with copper bromide, or copper chloride or copper sulfate and a butadiene to produce the substituted arylbutenyl chloride, (bromide) or (alcohol) which
(c) is then reacted with a suitable trisubstituted amine to produce the quaternary compound.

Illustrative of steps (a) and (b) is the following flow chart

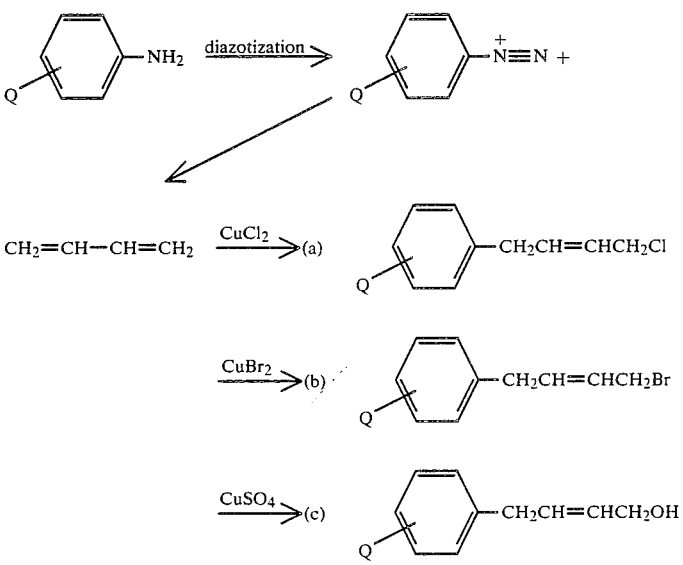

wherein Q is the equivalent of WXY.

Compounds (a) and (b) can be used to quaternize a trisubstituted amine to produce the compounds of this invention e.g.

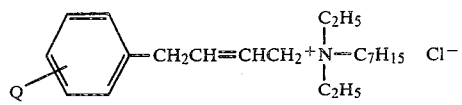

If it is desirable to change the anion, this may be done by commercially available ion exchange resins. As for instance, the above chloride anion may be exchanged in an anion exchange resin (e.g. Biorad AG 1-X8, 20-50 mesh, hydroxide form) and the resulting eluates titrated with 10% phosphoric acid to produce the $H_2PO_4^-$ anion.

In those instances, however, where Q (WXY) is defined as carbamoyl

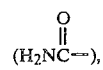

lower alkylureido

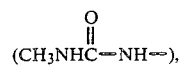

lower alkanoylamido

or lower alkanesulfonamido ($CH_3SO_2NH-$), a different approach to producing the compounds of this invention is used. For instance, one reacts 4-(4-chloro-2-butenyl)-1-nitrobenzene with diethylamine or a suitable secondary amine at a temperature of from about $-20°$ C. to about room temperature and reduces the reslting tertiary amine with iron in aqueous acid to give, for example, 4-(4-diethylamino-2-buten-1-yl)benzenamine. This aniline derivative is then acylated with lower alkanoyl halides (to produce amides), lower alkyl isocyanates or aryl isocyanates (to produce ureas), or lower alkanesulfonyl halides (to produce lower alkanesulfonamides) to give, for example, N,N-diethyl-4-(4-methanesulfonamidophenyl)but-2-en-1-amine which is then quaternized with a suitable alkyl halide, for example, 1-bromoheptane, to give N,N-diethyl-N-heptyl-4-(4-methanesulfonamido)phenyl-2-buten-1-aminium bromide.

In those instances where A is defined as

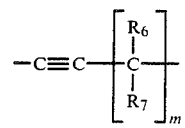

—an appropriately substituted benzaldehyde is reacted with bromomethyltriphenylphosphonium bromide in the presence of potassium tertiary butoxide to yield a substituted phenylacetylene. This compound is reacted with butyllithium and 2-chloroethyl-N,N-diethylamine to give the N,N-diethyl-4-(substituted phenyl)-3-butyn-1-amine, which is then quaternized with heptyl iodide.

Still further, in those instances where A is defined as

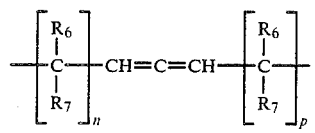

—a substituted benzaldehyde is reacted with trimethylsilylacetylene to give α-(2-trimethylsilylethynyl) substituted benzenemethanol. The alcohol function is then protected with a hydroxyl protecting group e.g. tetrahydropyranyl. The now hydroxyl protected compound is reacted with tetrabutylammonium fluoride and acetaldehyde to produce a compound of the following structure:

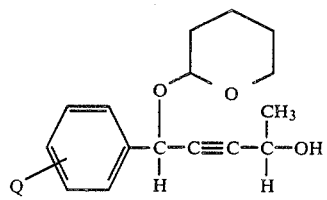

This compound is reacted with lithium aluminum hydride to produce 5-(substituted phenyl)-3,4-pentadiene-2-ol. This compound may be mesylated or tosylated and subsequently quaternized with N,N-diethylheptanamine to produce a compound of the formula:

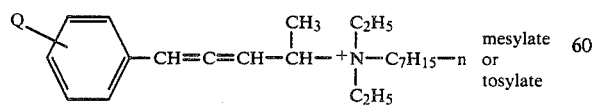

In addition to the novel compounds produced herein, a further aspect of this invention is a novel and expeditious method for the preparation of the known antiarrhythmic agent, clofilium, which is 4-chloro-N,N-diethyl-N-heptyl-benzenebutanaminium phosphate. Said process which is a variation of the process for producing the compounds of this invention, comprises the following steps:

(a) diazotization of para-chloroaniline to produce 4-chlorobenzenediazonium chloride, which is (b) reacted in a Meerwein arylation with butadiene to produce a mixture of 1-chloro-4-(4-chloro-2-butenyl)benzene and 1-chloro-4-(2-chloro-3-butenyl)benzene, which mixture is (c) used to quaternize N,N-diethyl-N-heptylamine, the resultant compound is (d) hydrogenated, followed by ion exchange to produce the subject compound.

Hydrogenation in the foregoing process is preferably carried out with rhodium on carbon in acetic acid or platinum on carbon in acetic acid or rhodium on carbon in dimethylformamide. A flow chart of the foregoing process is as follows:

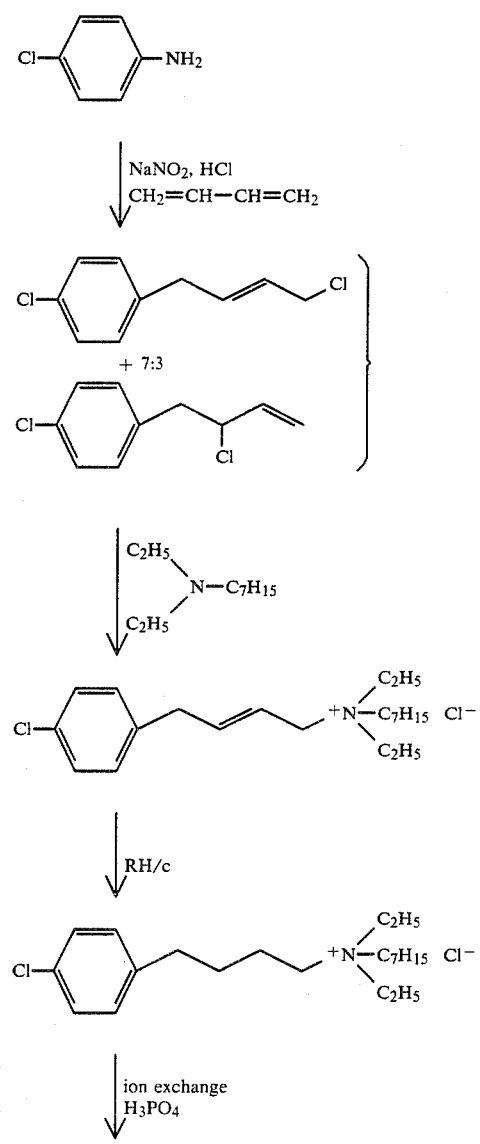

-continued

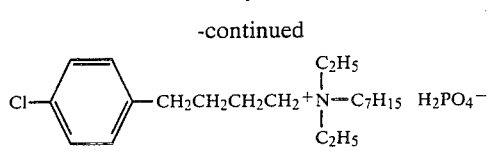

METHOD-OF-USE AND PHARMACEUTICAL

Composition Aspect

The compounds of this invention have been found to increase refractoriness of cardiac tissue thereby showing their usefulness as antiarrhythmic agents. Their activity has been analyzed in several procedures such as, utilizing standard electrophysiological techniques to measure resting potential, rate of rise, action potential amplitude, duration and effective refractory periods of normal canine Purkinje fibres; and also utilizing the programmed electrical stimulation conscious dog model.

Thus there is provided by this invention a method for treating arrhythmia which comprises administering to a subject suffering from an arrhythmia and in need of treatment or to a subject suspected of developing an arrhythmia, an effective amount for treating such arrhythmia of a compound of this invention. The compounds are preferably utilized for the control of reentrant arrhythmias in humans and for the prevention of sudden death resulting from ventricular fibrillation. Accordingly, it is contemplated that the compounds are best utilized in prophylactic treatment. Moreover, since the compounds enhance the electrical stability of the heart, they can be used in conjunction with electrical devices designed to terminate cardiac arrhythmias such as ventricular tachycardia and ventricular fibrillation.

In general, the compounds of this invention may be administered orally or parenterally. The dosage administered will be dependent on the subject being treated, the route of administration and the type and severity of the arrhythmia being prevented or reduced.

A typical dose for prophylactic treatment, however, will contain from about 0.5 mg/kg to about 5 mg/kg of the active compounds of this invention when administered orally. For I.V. administration, the dose will be from about 0.2 mg/kg to about 4 mg/kg, preferably about 0.2 to about 2 mg/kg.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain a compound of this invention for example, 4-(4-chlorophenyl)-N,N-diethyl-N-heptyl-2-buten-1-aminium phosphate in the amount of about 10 to about 50 mg. Such formulation can be administered orally at the rate of about 1 or 2 capsules per day or more often as needed depending upon the particular condition and subject being treated.

For parenteral administration a compound of this invention can be formulated for intramuscular or intravenous administration. In the case of treatment of a patient suffering from a severe cardiac arrhythmia, it may be desirable to administer a compound of the invention by intravenous infusion in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or saline solution, buffered aqueous solutions as well as dispersing and surface active agents if necessary. A typical formulation suited to intramuscular administration may contain a compound of this invention such as 4-(4-chlorophenyl)-N,N-diethyl-N-heptyl-2-buten-1-aminium phosphate in the amount of about 10 to 250 mg and a solubilizing agent and sufficient sterile water to bring the volume to about 2 ml. Such formulation can be injected at a rate of 1 to 4 times per day or more often depending upon the particular condition of the subject being treated.

The pharmaceutical preparations of the compounds of this invention may, optionally, contain one or more other pharmaceutically active substances. Some of the substances envisioned are vasodilators such as glycerol trinitrate, pentaerythritol tetranitrate and carbochromen; diuretic agents, such as chlorothiazide; heart tonics, such as digitalis preparations; hypotensive agents, such as Rauwolfia alkaloids and guanethidine; bronchodilators and sympathomimetic agents, such as isoprenaline, orciprenaline, adrenalin and ephedrine; α-adrenergic blocking agents, such as phentolamine; β-adrenergic blocking agents, such as propanolol; and other antiarrhythmic agents such as quinidine.

Other utilities may be ascribed to certain of the compounds of this invention, e.g., cardiotonic agents, bradycardic agents, antifungal agents and stabilizers for physiological formulations such as ophthalmic drops.

The invention described hereinabove is illustrated below in the Examples, which, however, is not to be construed as limiting the scope of this invention.

PREPARATIONS

Preparation 1 trans-4-(4'-Chlorophenyl)-3-buten-1-ol

To a suspension of triphenyl phosphine (2.1 g, 8.0 mmole) in 300 ml of triethylamine and 30 ml of acetonitrile under nitrogen is added successively palladium (II) acetate (0.45 g, 2.0 mmole), 1-bromo-4-chlorobenzene (19.1 g, 110 mmole) and 3-buten-1-ol (7.21 g, 100 mmole) in a pressure tube. The tube is sealed and heated in an oil bath to 100° C. for 24 hr. The tube is opened under nitrogen, charged with additional palladium (II) acetate, resealed and heated 20 hr longer at 100°–120° C. The mixture is cooled, vented to nitrogen and partitioned between 300 ml of 2N hydrochloric acid and ether. The layers are separated and the aqueous layer is extracted with two additional volumes of ether. The combined ether extracts are washed with 2×100 ml portions of 2N hydrochloric acid and then dried over sodium sulfate. The filtered ether extract is concentrated under vacuum to give 12.7 g of crude product which is purified by chromatography on silica gel using toluene eluent. There is obtained 9.5 g of the title compound. $R_f$=0.77 (silica gel, toluene).

Preparation 2

1-Chloro-3-(4-chloro-2-butenyl)benzene and 1-Chloro-3-(2-chloro-3-butenyl)benzene Treat 63.8 g (0.50 mole) of m-chloroaniline with a solution of 120 ml concentrated hydrochloric acid in 150 ml water and heat, with stirring, until dissolved. Chill the resulting solution to −9° C. To the resulting suspension add, dropwise, a solution of 35.2 g (0.51 mole) sodium nitrite in 100 ml water, keeping the internal temperature below −5° C. Stir the resulting solution for 1½ hrs at ca. −5° C. and filter to give a solution of the diazonium salt.

Combine a solution of 66.0 ml (0.76 mole) 1,3-butadiene in 500 ml acetone with a solution of 40.0 g (0.29 mole) sodium acetate trihydrate and 17.0 g (0.10 mole) cupric chloride hydrate in 80 ml water. Chill the resulting heterogeneous mixture to −5° C. and treat it slowly with the solution of the diazonium salt (also kept at −5° C.) with rapid stirring. Stir the resulting solution for 17 hrs at room temperature. Add 500 ml ether and stir for 15 minutes. Separate the layers. Wash the organic layer with 3×300 ml water, dry over magnesium sulfate, filter and evaporate off the solvents in vacuo. Purify through a silica gel column, eluting with methylene chloride to provide the title compounds in a ratio of 4:3 based on NMR interpretation.

1-Chloro-3-(4-chloro-2-butenyl)benzene

NMR(CDCl$_3$): $\delta$ = 3.30(d,2), 4.00(d,2), 5.50–6.20(m,2) and 6.90–7.50(m,4)ppm.

1-Chloro-3-(2-chloro-3-butenyl)benzene

NMR(CDCl$_3$): $\delta$ = 3.10(d,1.5), 4.50(quar.,0.75), 5.00–6.20(m,2.3) and 6.90–7.50(m,3)ppm.

PREPARATION 3

1-Chloro-4-(4-chloro-2-butenyl)benzene and 1-Chloro-4-(2-chloro-3-butenyl)benzene [7:3]

To 114.18 g (0.895 moles) of 4-chloroaniline add with stirring 400 ml 6N HCl. Reflux the reaction mixture for 20 minutes and then cool to 0° C. Add dropwise, a solution of 61.4 g sodium nitrite in 90 ml H$_2$O keeping the reaction mixture at −10° C. and continue stirring at that temperature for 40 minutes.

Add the diazonium reaction mixture to a mixture containing 120 ml 1,3-butadiene, 1500 ml acetone, 32.90 g CaO, 27.6 g copper (II) chloride and 90 ml H$_2$O which is kept at −20° C. with dry ice/acetone bath. Bubble butadiene through the reaction mixture and allow the temperature to warm to +5° C. Keep temperature of reaction mixture between +5–(+10)° C. for ca. one hour by which time N$_2$ evolution ceases. Warm reaction mixture to room temperature and extract with 3×600 ml Et$_2$O. Wash organic layer with 3×400 ml saturated NaCl solution. Add 500 g silica gel and stir for 1½ hours. Filter and evaporate solvent to yield a liquid. Distill in vacuo to provide the title compounds in 84% yield.

Preparation 4

N,N-Diethyl-1-heptanamine

Dissolve 50.90 ml (0.5 moles) diethylamine and 57.10 g (0.5 mole) heptaldehyde in 500 ml methanol and stir at room temperature for one hour. Slowly add 31.42 g sodium cyanoborohydride in 500 ml methanol to the stirred reaction mixture. Add glacial acetic acid to the reaction mixture until pH=6. Stir at room temperature overnight. Concentrate reaction mixture volume to 300 ml and then add 500 ml distilled water. Add concentrated hydrochloric acid until pH=1. Extract with 5×250 ml methylene chloride. Evaporate organic solvent and then dissolve the residue in 400 ml 0.1N HCl. Wash aqueous solution with 3×200 ml diethyl ether and then add 2N NaOH until solution is basic (pH=12). Extract with 3×200 ml diethyl ether. Dry over MgSO$_4$, filter and evaporate, the distill in vacuo to obtain 46.0 g (53.7%) title compound.

PREPARATION 5

N,N-Diethyl-4-(4-nitrophenyl)-2-buten-1-amine hydrochloride

To 250 ml of diethylamine at 0° C. add 30 g (0.14 mole) of 1chloro-4-(4-nitrophenyl)-2-butene over a 30 minute period. Stir for 16 hr at room temperature. Remove the solvent in vacuo. Extract the residue with 200 ml of 10% hydrochloric acid. Extract the resulting solution 2×100 ml ethyl acetate and discard. Adjust the pH of the water layer to about 12 with 10% sodium hydroxide. Extract 3×100 ml methylene chloride. Take the combined organic extracts and dry over Na$_2$SO$_4$. Remove the solvent in vacuo. Dissolve the residue in 100 ml ethanol, and add 1.5 equivalents of concentrated hydrochloric acid. Evaporate off the solvent, and crystallize the residue with acetone to provide the title compound.

NMR(CD$_3$OD): $\delta$ = 1.15–1.65(t,6), 3.0–3.55(quar,4), 3.55–4.0(m,4), 5.5–6.65(m,2), 7.4–7.75(m,2) and 8.1–8.45(m,2)ppm.

PREPARATION 6

N,N-Diethyl-4-(4-aminophenyl)-2-buten-1-amine

To a solution of 25 g (0.45 mole) of iron filings in 200 ml acetic acid, add a solution of 8.5 g (0.03 mole) N,N-diethyl-4-(4-nitrophenyl)-2-buten-1-amine hydrochloride in 50 ml water. Temperature rises to about 40° C., stir for 2 hr then filter off the excess iron. Adjust the pH of the filtrate to about 12 with sodium hydroxide, and extract with 3×100 ml methylene chloride. Take the combined extracts, dry over Na$_2$SO$_4$, then treat with charcoal. Evaporate the solvent to provide the title compound.

NMR(CDCl$_3$): $\delta$ = 0.95–1.3(t,6), 2.35–2.85(quar,4), 2.95–3.2(d,2), 3.2–3.45(d,2), 3.45–3.7(bs,2), 5.5–5.85(m,2) and 6.65–7.15(m,4)ppm.

PREPARATION 7

(E)-4-(4-Chlorophenyl)-N,N-diethyl-2-buten-1-amine

Add 30 ml diethylamine to 10.0 g (0.05 mole) of a 7:3 mixture of (E)-1-chloro-4-(4-chloro-2-butenyl)benzene and 1-chloro-4-(2-chloro-3-butenyl)benzene and stir at room temperature overnight. Dissolve reaction mixture in 100 ml 1N HCl and wash with 50 ml ethyl acetate. Extract ethyl acetate layer with 50 ml 1N HCl. Combine aqueous layers and add cold 4N NaOH until solution has pH=9. Extract aqueous phase with 5×60 ml Et$_2$O. Dry ethereal extracts over Na$_2$SO$_4$ and then filter. Evaporate solvent to provide the title compound.

NMR(CDCl$_3$): $\delta$ = 1.02(t,6), 2.56(q,4), 3.06(d,2), 3.22(d,2), 5.18–6.03(m,2) and 7.00–7.42(m,4)ppm.

PREPARATION 8

4-Chloro-N,N-diethylbenzenebutanamine

Add 2.0 g (0.0084 mole) of (E)-4-(4-chlorophenyl)-N,N-diethyl-2-buten-1-amine to flask containing 0.20 g platinum (5%) on activated charcoal suspended in 15 ml glacial acetic acid. Stir reaction mixture under one atmosphere hydrogen until hydrogen absorption ceases (4½ hours). Filter reaction mixture with methylene chloride wash and 50 ml distilled water. Separate layers and extract aqueous with 3×70 ml methylene chloride. Combine methylene chloride extracts and wash with cold 2×75 ml 1N NaOH. Dry organic layer over $MgSO_4$, filter and evaporate to yield the title compound.

NMR($CDCl_3$): $\delta = 1.05(t,6)$, 1.40–1.95(m,4), 2.62(q,8) and 7.10–7.55(m,4)ppm.

PREPARATION 9

1-Chloro-4-(2-propynyl)benzene

Place 59 g (2.43 mole) of magnesium turnings into a four-neck flask equipped with mechanical stirrer under $N_2$ atmosphere. Add 500 ml of anhydrous ether and then add a solution of 465 g (2.43 mole) of 1-bromo-4-chlorobenzene in 1000 ml of anhydrous ether dropwise while stirring. Stir one hour after the completion of addition. Transfer and add this Grignard reagent to a solution of 170 g (2.43 mole) of 1-methoxy-1,2-propanediene and 69 g of copper (I) bromide in 300 ml of anhydrous ether with cooling. Stir for another ten minutes after the completion of addition. Add saturated aqueous solution of ammonium hydroxide and decant ether solution. Wash the solid residue with ether (3×50 ml). Wash the combined ether solutions with 1N HCl, saturated aqueous sodium bicarbonate, and with $H_2O$. Dry over magnesium sulfate, evaporate, and distill in vacuo to yield the title compound, b.p. 99°–105° C. (15 mmHg).

NMR($CDCl_3$): $\delta = 2.20(t,1)$, 3.59(d,2) and 7.30(s,4)ppm.

PREPARATION 10

1-(4-Chlorophenyl)-2-butyn-1-ol

Dissolve 150.6 g (1.00 mole) of 1-chloro-4-(2-propynyl)benzene in 600 ml of anhydrous ether under $N_2$ atmosphere with stirring at dry ice/acetone temperature. Add dropwise a solution of 400 ml of n-butyllithium (2.5M in hexane) (1.00 mole). Stir for an additional 30 minutes after completion of addition. Add 31 g (1.00 mole) of paraformaldehyde. Stir the mixture at dry ice/acetone temperature for 1 hour, and allow to warm to room temperature. Follow the progress of the reaction by thin-layer chromatography on silica gel (methylene chloride). At the completion of the reaction, add 400 ml of saturated aqueous sodium chloride, separate layers, and extract aqueous layer with ether (2×100 ml). Wash the combined ether solutions with water, dry over magnesium sulfate and evaporate. Triturate the oil residue with petroleum ether to provide the title compound.

NMR($CDCl_3$): $\delta = 2.72(s,1)$, 3.57(t,2), 4.27(t,2) and 7.27(s,4)ppm.

PREPARATION 11

(Z)-4-(4-Chlorophenyl)but-2-en-1-ol

Dissolve 10 g (0.055 mole) of 4-(4-chlorophenyl)but-2-yn-1-ol in 100 ml of acetone. Add 0.6 g of Lindlar's catalyst. Stir the mixture under 1 atmosphere of hydrogen at room temperature. Follow the progress of the reaction by NMR. At the completion of the reaction, filter to remove the catalyst and evaporate to yield the title compound.

PREPARATION 12

(Z)-4-(4-Chlorophenyl)but-2-en-1-ol 4-methylbenzenesulfonate

Dissolve 7.3 g (0.04 mole) of (Z)-4-(4-chlorophenyl)-but-2-en-ol in 100 ml of anhydrous ether. Add 3.2 g (0.05 mole) of powdered 86% KOH. Stir and cool the mixture in ice bath while adding a solution of 8.4 g (0.044 mole) of p-toluenesulfonyl chloride in 50 ml of anhydrous ether. Slowly warm the reaction mixture to room temperature and stir at room temperature for 16 hours. Remove the solid by filtration. Wash the filtrate with saturated aqueous sodium bicarbonate, $H_2O$. Dry, evaporate, and recrystallize from cyclohexane to yield the title compound.

EXAMPLES

EXAMPLE 1

N,N-Diethyl-4-(2,3-dichlorophenyl)-N-heptyl-2-buten-1-aminium 4-methylbenzenesulfonate 3.61 g (0.021 mole) N,N-Diethyl-1-heptanamine and 5.0 g (0.021 mole) 1,2-dichloro-3-(4-chloro-2-butenyl)-benzene are heated at 140° C. for ca. 8 hrs, and allowed to stand at room temperature for 72 hrs. The reaction mixture is taken up in 50 ml $H_2O$ and 20 ml ether, a 3-layer system results. The aqueous layer and the insoluble material are combined and extracted with 75 ml $CH_2Cl_2$. The $CH_2Cl_2$ layer is washed with 5×50 ml 5% HCl. The solvent is removed from the $CH_2Cl_2$ layer, and the resulting oil is triturated with 3×100 ml $Et_2O$. The resulting oil is applied to an anion exchange column (23 g resin AG1-X8 hydroxide form, 20–50 mesh which has been stirred in 1M NaOH for 30 min, poured into a column, and washed with deionized $H_2O$ until the pH of the eluate=7). The column is eluted with deionized water until the pH of the fractions reaches about 8. The fractions are chilled as collected. The basic fractions are neutralized by addition of a concentrated aqueous solution of p-toluenesulfonic acid. The resulting aqueous suspension is extracted with 3×75 ml $CH_2Cl_2$; the organic layers are pooled, dried over $MgSO_4$, filtered, and evaporated to yield the title compound.

NMR($CDCl_3$): $\delta = 0.60–1.77(m,19)$, 2.35(s,3), 2.75–3.70(m,8), 3.85(d,2), 5.35–6.50(m,2), 6.90–7.62(m,5) and 7.63–7.92(d,2)ppm.

EXAMPLE 2

N,N-Diethyl-4-(2-chlorophenyl)-N-heptyl-2-buten-1-aminium chloride

Combine 1.00 g (4.76 mmole) 1-chloro-2-(4-chloro-2-butenyl)benzene and 1.77 g (4.76 mmole) N,N-diethyl-heptanamine and heat at 100° C. ca. 20 hrs. Follow the progress of the reaction by TLC on silica gel (acetonitrile: ammonium hydroxide, 9:1). At the completion of the reaction, decant off the top layer of the two phase reaction mixture. Dissolve the bottom layer in 50 ml $H_2O$. Extract with 3×100 ml hexane, 1×25 ml $CH_2Cl_2$. Dry $CH_2Cl_2$ over $MgSO_4$ and treat with activated charcoal. Evaporate the solvents to provide the title compound.

NMR(CDCl₃): δ=0.55–2.00(m,19), 2.75–3.75(m,8), 3.65–4.35(d,2), 5.95–6.70(m,2) and 7.0–7.65(m,4)ppm.

EXAMPLE 3

(E)-4-(4-Chlorophenyl)-N,N-diethyl-N-heptyl-2-buten-1-aminium chloride

Dissolve 35.55 g (0.1768 mole) of a mixture of 1-chloro-4-(4-chloro-2-butenyl)benzene and 1-chloro-4-(2-chloro-3-butenyl)benzene and 27.7 g (0.1607 mole) of N,N-diethyl-1-heptanamine in 220 ml of acetonitrile. Heat the reaction mixture to reflux for 6 hours. Follow the progress of the reaction by thin layer chromatography (acetonitrile: ammonium hydroxide, 95:5). At the completion of the reaction, evaporate solvent and dissolve the residue in 400 ml distilled water. Add solid sodium bicarbonate until pH of solution is 8.5. Wash the aqueous mixture with 4×200 ml petroleum ether and then 5×200 ml Et₂O. Add 1N HCl to aqueous layer until pH=1 and then extract with 3×200 ml methylene chloride. Dry over magnesium sulfate, filter and evaporate solvent. Dissolve the material in 150 ml of 2-butanone and then add diethyl ether until solution becomes cloudy. Warm solution until clear and then cool and store in freezer for 3 hours to complete crystallization and then filter title compound. Recrystallize a second time (2-butanone/ether) to provide the title compound in 60% yield.

EXAMPLE 4

(E)-4-(4-Chlorophenyl)-N,N-diethyl-N-heptyl-2-buten-1-aminium dihydrogenphosphate Dissolve 5.92 g (0.016 mole) of (E)-4-(4-chlorophenyl)-N,N-diethyl-N-heptyl-2-buten-1-aminium chloride in water and pour onto column containing 20 g anion exchange resin (hydroxide form BIO-RAD AG-1-X8). Elute sample through column with water and collect eluent having pH>9. Wash this aqueous solution with methylene chloride. Titrate aqueous layer to pH=6 with 20% phosphoric acid and from pH=6 to pH=4.5 with 5% phosphoric acid (v/v). Lyophilize aqueous solution to dryness and then triturate with diethyl ether to provide the title compound.

NMR(D₂O): δ=0.57–1.78(m,19), 2.68–3.94(m,10), 5.50–6.50(m,2) and 7.30(s,4)ppm.

EXAMPLE 5

4(3-Chlorophenyl)-N,N-diethyl-N-heptyl-2-buten-1-aminium chloride

Heat a mixture of 6.0 g (0.03 mole) of 1-chloro-3-(4-chloro-2-butenyl)benzene and 3-chloro-4-(3-chlorophenyl)-1-butene (in a ratio of 4:3) and 5.1 g (0.03 mole) N,N-diethylheptanamine at 100° C. for about 20 hours. Dissolve in 100 ml water and wash with 3×75 ml hexane and then extract with methylene chloride. Dry methylene chloride extract over magnesium sulfate, filter and evaporate the solvent in vacuo to provide the title compound.

EXAMPLE 6

4-Chloro-N,N-diethyl-N-heptylbenzenebutanaminium dihydrogenphosphate

Add 2.1 g (5.6 mmole) of (E)-4-(4-chlorophenyl)-N,N-diethyl-N-heptyl-2-buten-1-aminium chloride to a suspension of 0.11 g catalyst (rhodium (5%) on carbon) in 100 ml glacial acetic acid and stir under 1 atmosphere hydrogen for 19 hours at room temperature. Filter through celite and then wash celite with 100 ml H₂O. Combine filtrates and extract into 4×100 ml methylene chloride. Wash methylene chloride extracts with 1×100 ml 1N HCl, 2×250 ml saturated aqueous sodium bicarbonate and 200 ml saturated aqueous sodium chloride. Dry methylene chloride over sodium sulfate, filter and evaporate solvent to provide 4-chloro-N,N-diethyl-N-heptylbenzenebutanaminium chloride. Dissolve product in 75 ml H₂O/MeOH (50:50) and pour onto column containing 6 g anion exchange resin (hydroxide form BIO-RAD AG-1-X8). Elute sample through column with distilled water and collect eluate having pH≧9. Wash this aqueous solution with 2×150 ml methylene chloride. Titrate sample to pH=5.0 with 10% phosphoric acid and to pH=4.5 with 0.1N phosphoric acid. Evaporate to provide 1.25 (51%) of title compound.

EXAMPLE 7

(Z)-4-(4-Chlorophenyl)-N,N-diethyl-N-heptyl-2-buten-1-aminium 4-methylbenzenesulfonate Mix 5.40 g (0.016 mole) of (Z)-4-(4-chlorophenyl)but-2-en-1-ol 4-methylbenzenesulfonate and 10.96 g (0.064 mole) of N,N-diethylheptanamine in 200 ml of acetonitrile. Stir the mixture at room temperature for 2 hours. Evaporate and recrystallize from ethyl acetate to yield the title compound, m.p. 79°–80° C.

NMR(CDCl₃): (300 MHz)δ=0.88(t,3), 1.24(br s,8), 1.34(t,6), 1.64(br s,2), 2.32(s,3), 3.5–3.6(m,2), 3.43(q,4), 3.55(d,2), 4.22(d,2), 5.51–5.66(m,1), 6.08–6.22(m,1), 7.05(2d,4), 7.25(d,2) and 7.78(d,2)ppm.

EXAMPLE 8

N-[4-[4-(Diethylamino)-2-butenyl]phenyl]methanesulfonamide

Dissolve 3.5 g (0.014 mole) N,N-diethyl-4-(4-aminophenyl)-2-buten-1-amine in 50 ml of methylene chloride, chill to about 0° C. To this slowly add 1.5 ml (0.019 mole) of methanesulfonyl chloride. Stir at room temperature 1 hr and then wash with 2×50 ml of 10% NaOH. Wash the sodium hydroxide extracts with 1×100 ml of ether and then acidify to pH 10 with concentrated HCl. Extract with 2×100 ml methylene chloride and dry the methylene chloride extracts over Na₂SO₄. Evaporate to dryness to yield the title compound.

NMR(CDCl₃): δ=0.9–1.3(t,6), 2.4–2.8(quar,4), 3.0–3.3(m,5), 3.3–3.5(d,2), 5.6–5.9(m,2), 7.0(s,1) and 7.1–7.3(m,4)ppm.

EXAMPLE 9

N,N-Diethyl-N-heptyl-4-(4-methanesulfonamidophenyl)-2-buten-1-aminium methanesulfonate Combine 3.0 g (0.01 mole) of N-[4-[4-(diethylamino)-2-butenyl]phenyl]methanesulfonamide and 20 ml of iodoheptane and heat to about 70°–80° C. for 24 hours. Cool to room temperature and triturate with 5×100 ml portions of ether. Discard the ether portions, and dissolve the residue in 20 ml of a 1:1 methanol/water solution. Pass through 30 g of anion exchange resin (−OH form), and wash with 1:1 methanol/water until pH of eluate is about 8. Remove methanol under vacuum. Extract the aqueous portion with 2×100 ml ether, and discard the ether. Acidify the aqueous portion to pH=4.5 with methanesulfonic acid. Remove the water under vacuum at 50° C. Crystallize the residue from acetone/ether to provide the title compound.

NMR(CDCl₃): δ=0.6-1.9(m,21), 2.2(s,3), 2.7(s,3), 2.9-3.6(m,10), 3.8-4.1(d,2), 4.3-5.0(m,1), 5.3-6.5(m,2) and 6.9-7.5(m,4)ppm.

We claim:

1. A compound of the following general formula:

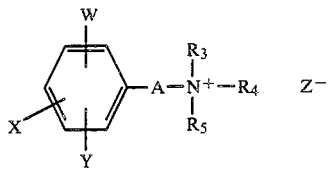

wherein
A is

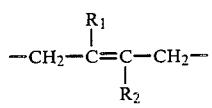

R₁, R₂ are both hydrogen or both C₁-C₂ alkyl, or when taken together are —(CH₂)₃— or —(CH₂)₄— to form the cyclopentene or cyclohexene moiety;

R₃, R₄ are both C₁-C₄ alkyl;

R₅ is C₅₋C₁₀ alkyl, phenyl C₁-C₄ alkyl or cycloalkyl lower alkyl;

W, X, Y are the same or independently hydrogen, hydroxy, halogen, cyano, trifluoromethyl, carbamoyl, C₁-C₄ alkoxy, lower alkoxycarbonyl, N-lower alkylcarbanoyl, lower alkanoylamido, lowr alkanesulfonamido, lower alkylsulfonyl, sulfamoyl, lower alkanesulfamoyl, or N-lower alkylureido;

with the provisos that:
(a) only one of W, X and Y can be cyano or trifluoromethyl;
(b) only two of W, X and Y can simultaneously be hydroxy;
(c) at least one of W, X and Y is other than hydrogen;
and Z⁻ is a therapeutically acceptable anion.

2. A compound of claim 1 wherein A is a 4 carbon chain.

3. A compound of claim 1 wherein two of W,X and Y are hydrogen.

4. A compound of claim 3 wherein W and Y are hydrogen and X is a substituent in the para position.

5. A compound of claim 3 wherein one of W,X and Y is halogen.

6. A compound of claim 3 wherein one of W,X and Y is lower alkanesulfonamido.

7. A compound of claim 3 wherein one of W,X and Y is N-lower alkylureido.

8. A compound of claim 3 wherein one of W,X and Y is sulfamoyl.

9. A compound of claim 1 wherein R₅ is C₅-C₁₀ alkyl.

10. A compound of claim 1 wherein R₃ and R₄ are methyl or ethyl and R₅ is —(CH₂)₆CH₁₃.

11. A compound of claim 10 wherein A is —CH₂—CH=CH—CH₂—.

12. A compound of claim 11 wherein two of W,X and Y are hydrogen.

13. A compound of claim 12 wherein W and Y are hydrogen and X is a substituent in the para position.

14. A compound of claim 13 which is 4-(4-chlorophenyl)-N,N-diethyl-N-heptyl-2-buten-1-aminium dihydrogenphosphate.

15. A compound of claim 13 which is (E)-(4-chlorophenyl)-N,N-diethyl-N-heptyl-2-buten-1-aminium dihydrogenphosphate.

16. A compound of claim 13 which is (Z)-(4-chlorophenyl)-N,N-diethyl-N-heptyl-2-buten-1-aminium 4-methylbenzenesulfonate.

17. A compound of claim 13 which is N,N-diethyl-N-heptyl-4-(4-trifluoromethylphenyl)-2-buten-1-aminium chloride.

18. A compound of claim 13 which is N,N-diethyl-N-heptyl-4-(4-sulfamoylphenyl)-2-buten-1-aminium chloride.

19. A compound of claim 13 which is 4-(4-cyanophenyl)-N,N-diethyl-N-heptyl-2-buten-1-aminium chloride.

20. A compound of claim 13 which is N,N-diethyl-N-heptyl-4-(4-methoxycarbonylphenyl)-2-buten-1-aminium chloride.

21. A compound of claim 13 which is N,N-diethyl-N-heptyl-4-(4-methylsulfonylphenyl)-2-buten-1-aminium chloride.

22. A compound of claim 12 which is 4-(3-chlorophenyl)-N,N-diethyl-N-heptyl-2-buten-1-aminium chloride.

23. A compound of claim 12 which is 4-(2-chlorophenyl)-N,N-diethyl-N-heptyl-2-buten-1-aminium chloride.

24. A compound of claim 12 which is N,N-diethyl-N-heptyl-4-(4-methanesulfonamidophenyl)-2-buten-1-aminium chloride.

25. A compound of claim 11 which is 4-(2,3-dichlorophenyl)-N,N-diethyl-N-heptyl-2-buten-1-aminium 4-methylbenzenesulfonate.

26. A compound of claim 1 which is N,N-diethyl-N-heptyl-4-(4-chlorophenyl)-2,3-dimethyl-2-buten-1-aminium chloride.

27. A compound of claim 12 which is N,N-diethyl-N-heptyl-4-[4-(3-methyl-1-uriedo)phenyl]-2-buten-1-aminium chloride.

28. The method for the treatment of cardiac arrhythmia in a mammalian subject which comprises administering to said subject an amount effective for the suppression of said arrhythmia of a compound according to claim 1.

29. A pharmaceutical composition for the treatment of cardiac arrhythmia comprising an antiarrhythmic effective amount of a compound of claim 1 together with a non-toxic pharmaceutically acceptable carrier.

* * * * *